United States Patent
Brandstätter et al.

(10) Patent No.: US 7,380,986 B2
(45) Date of Patent: Jun. 3, 2008

(54) X-RAY APPARATUS AND MAMMOGRAPHIC X-RAY APPARATUS WITH AN INDICATOR

(75) Inventors: Werner Brandstätter, Nürnberg (DE); Martin Ramsauer, Pyrbaum (DE)

(73) Assignee: Siemens Aktiengesellschaft, Munich (DE)

( * ) Notice: Subject to any disclaimer, the term of this patent is extended or adjusted under 35 U.S.C. 154(b) by 65 days.

(21) Appl. No.: 10/591,980

(22) PCT Filed: May 4, 2005

(86) PCT No.: PCT/EP2005/052047

§ 371 (c)(1),
(2), (4) Date: Sep. 6, 2006

(87) PCT Pub. No.: WO2005/110233

PCT Pub. Date: Nov. 24, 2005

(65) Prior Publication Data

US 2007/0183565 A1    Aug. 9, 2007

(30) Foreign Application Priority Data

May 11, 2004    (DE) .................. 10 2004 023 046

(51) Int. Cl.
*A61B 6/08*    (2006.01)

(52) U.S. Cl. ........................ 378/206; 378/37

(58) Field of Classification Search ........... 378/37, 378/205, 206
See application file for complete search history.

(56) References Cited

U.S. PATENT DOCUMENTS

| | | | |
|---|---|---|---|
| 4,259,585 A * | 3/1981 | Novak et al. ............. | 378/37 |
| 4,825,455 A | 4/1989 | Bauer et al. | |
| 5,553,115 A * | 9/1996 | Odaka et al. ............. | 378/206 |
| 5,563,924 A | 10/1996 | Winkelman | |
| 5,600,698 A * | 2/1997 | Terashima et al. ....... | 378/206 |
| 6,036,362 A * | 3/2000 | Schmitt .................... | 378/206 |
| 6,104,778 A | 8/2000 | Murad | |
| 6,305,842 B1 | 10/2001 | Kunert | |
| 6,435,717 B1 | 8/2002 | Köhler et al. | |

FOREIGN PATENT DOCUMENTS

| | | |
|---|---|---|
| DE | 199 43 898 A1 | 3/2001 |
| EP | 0 819 407 A1 | 1/1998 |

* cited by examiner

*Primary Examiner*—Chih-Cheng G Kao
(74) *Attorney, Agent, or Firm*—Brinks, Hofer, Gilson & Lione

(57) ABSTRACT

An X-ray apparatus and a mammographic X-ray apparatus are provided. The X-ray apparatus includes an X-ray beam generated by an X-ray source and a diaphragm. At least one LED is disposed as an indicator between the X-ray source and the diaphragm. The illuminating beam of the LED is directed in an undeflected fashion onto the X-ray field. The LED may be pivotable (swivable) out of the X-ray beam. The LED is mounted on a filter array that is mounted between the X-ray source and the diaphragm.

7 Claims, 3 Drawing Sheets

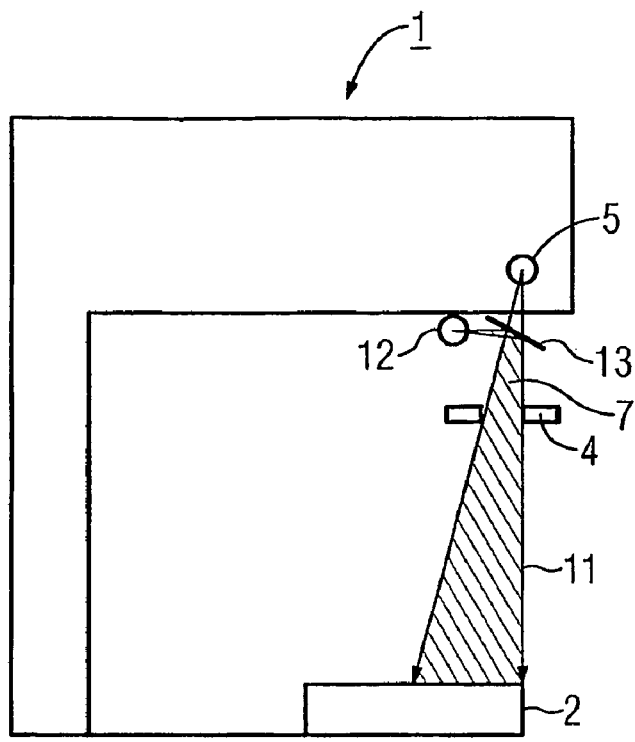
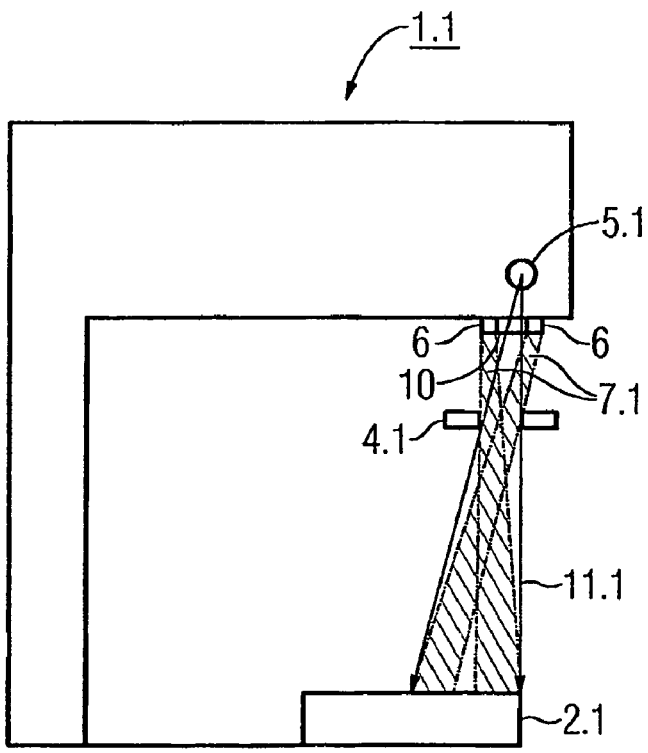

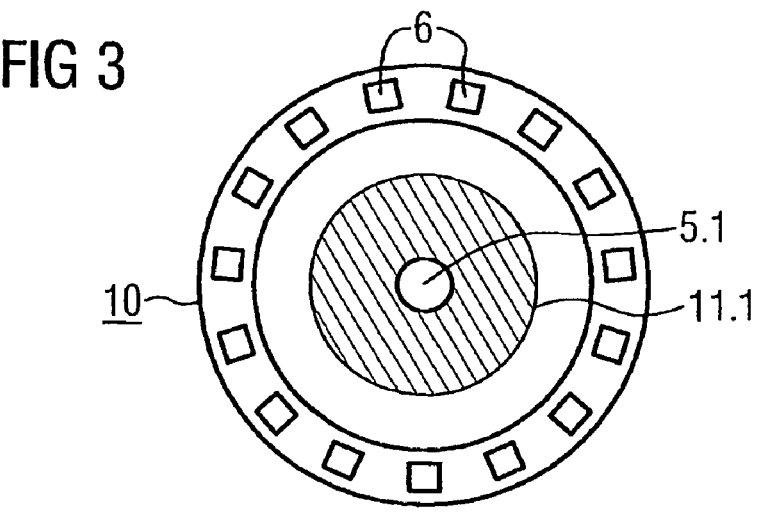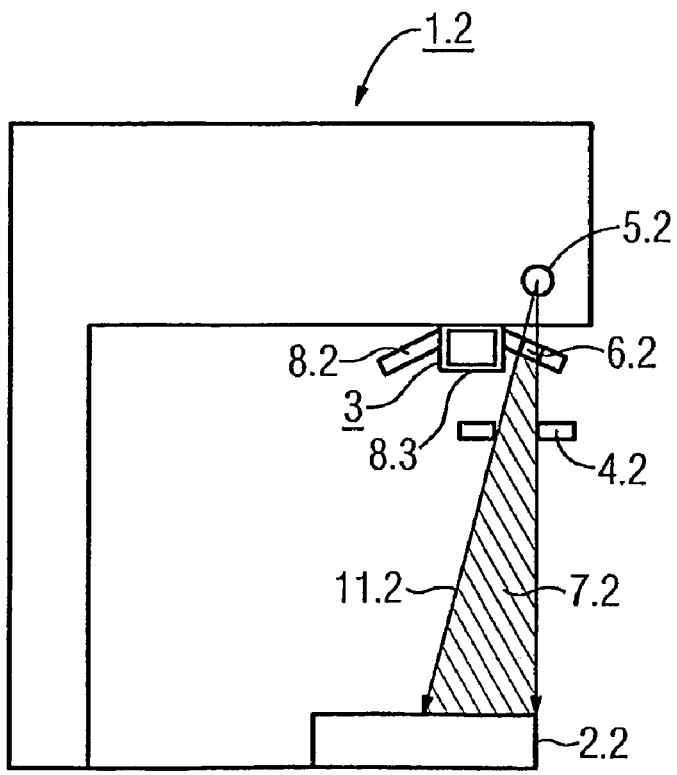

X-RAY APPARATUS AND MAMMOGRAPHIC X-RAY APPARATUS WITH AN INDICATOR

The present patent document is a continuation of PCT Application Serial Number PCT/EP2005/052047, filed May 4, 2005, designating the United States, which is hereby incorporated by reference. The present patent document also claims the benefit of foreign application number DE 10 2004 023 046.3 filed on May 11, 2004, which is hereby incorporated by reference.

BACKGROUND

1. Field

The present embodiments relate to an X-ray apparatus, such as a mammographic X-ray apparatus. The apparatus includes an indicator.

2. Related Art

Generally, mammographic X-ray apparatuses have an indicator. Before the actual process of taking the X-ray images, the indicator projects an exemplary trace of an X-ray field on the surface of a patient body and/or on an object table. The X-ray field is monitored, for example, to assure that the correct diaphragm has been chosen. Conventionally, an incandescent bulb mounted laterally of the X-ray beam path is used. The beam of light from the incandescent bulb that extends perpendicular to the X-ray beam path, is deflected into the direction of the X-ray beam by a mirror disposed in the X-ray beam path. During the actual taking of the X-ray image, the mirror is folded out of the way of the beam path, or if it is radiotransparent, it stays in the beam path.

An X-ray apparatus of this kind is known from German Patent Disclosure DE 199 43 898 A1. According to DE 199 43 898 A1, an indicator in the form of laser diodes have been previously used, for example, for X-ray apparatuses used as aids in surgery. The indicators are mounted either on the X-ray detector or on the X-ray source. Accordingly, the region through which the X-radiation passes, for example, above the surface of the patient and/or the X-ray field on the surface of the patient, is visible (illuminated). The indicator is designed to be adaptable to the geometry of the X-ray beam, for example, the size of the opening angle, for instance by sending a signal for changing the aperture of the diaphragm onward to the indicator.

SUMMARY

The present embodiments relate to an X-ray apparatus and a mammographic X-ray apparatus with an indicator. The present embodiments may obviate one or more of the problems due to the limitations and disadvantages of the related art. For example, one exemplary embodiment illuminates the X-ray field, which precedes the actual making of the X-ray, in a way that is simple and involves little effort.

In one exemplary embodiment, an X-ray apparatus includes an X-ray beam generated by an X-ray source and a diaphragm. At least one LED is disposed as an indicator between the X-ray source and the diaphragm. The illuminating beam of the at least one LED is directed in an undeflected fashion onto the X-ray field, and the at least one LED is pivotable (swivable) out of the X-ray beam. The at least one LED is mounted on a filter array that is mounted between the X-ray source and the diaphragm. Accordingly, the diaphragm may not be used for shaping the beam of the X-ray beam and shaping the beam of the illuminating beam, and thus deflecting the illuminating beam can be eliminated. Complicated control of the orientation of the indicator means is eliminated, and a mirror that can be folded away is unnecessary, making a compact, low-maintenance construction possible.

In one exemplary embodiment, at least one LED is mounted on a filter array that is associated with the X-ray apparatus and is located between the X-ray source and the diaphragm. In most X-ray apparatuses (systems), the filter array is fundamentally present. All that is needed is a mount for the LED. Alternatively, the LEDs are disposed on a common ring mount, in a way that is expedient for simple mounting if there is a plurality of LEDs surrounding the X-ray beam.

DRAWINGS

FIG. 1 illustrates a side view of a known mammographic X-ray apparatus with an incandescent bulb and deflection mirror that illuminates an X-ray field;

FIG. 2 illustrates a side view of a mammographic X-ray apparatus with a plurality of LEDs on a ring mount for illuminating the X-ray field according to an exemplary embodiment;

FIG. 3 illustrates an exemplary ring mount;

FIG. 4 illustrates a side view of a mammographic X-ray apparatus having at least one LED on a filter array for illuminating the X-ray field according to an exemplary embodiment;

DETAILED DESCRIPTION

Figure 5:
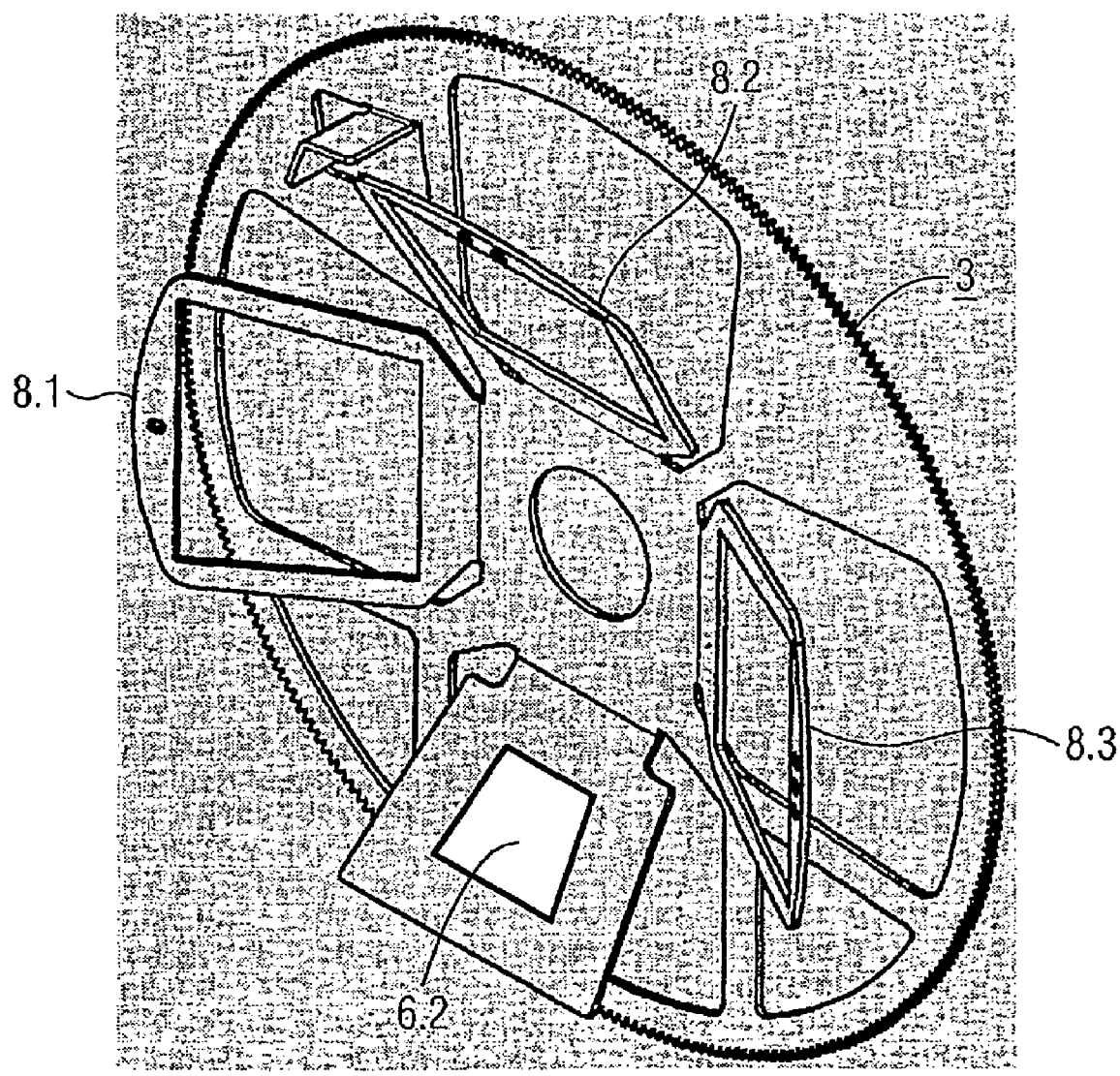
FIG. 5 illustrates a filter array with at least one LED according to one exemplary embodiment.

FIG. 1 shows a mammographic X-ray apparatus 1 according to the prior art. The mammographic X-ray apparatus 1 includes both an X-ray source 5 and a detector, for example, an object table 2 equipped with an X-ray film. During an examination, the X-ray source 5 generates an X-ray beam 11 that projects an object (image) (not shown), of a patient, which is to be examined, onto the detector. The mammographic X-ray apparatus 1 includes a diaphragm 4 that limits the X-ray beam 11 by blanking out, collimating, or blocking some portions of the X-ray beam 11. Before an actual operation of making an X-ray image, an X-ray beam location on the surface of the patient or on the object table 2 is monitored by an illuminating beam 7 that is generated by an incandescent bulb 12. The illuminating beam 7 is deflected by a mirror 13 in the direction of the X-ray field. The incandescent bulb 12 and the mirror 13 are adjusted, so that the illuminating beam 7 and the X-ray beam 11 are substantially congruent on the surface of the patient or on the object table 12. In one exemplary embodiment, the mirror 13 is radiotransparent in order not to hinder the X-ray beam 11. Alternatively, the mirror 13 can be folded out of the way of the X-ray beam 11.

FIG. 2 shows a different embodiment of a mammographic X-ray apparatus 1.1. The mammographic apparatus 1.1 includes a plurality of LEDs 6 disposed between an X-ray source 5.1 and a diaphragm 4.1. The illuminating beam 7.1 is directed onto the X-ray field. In one exemplary embodiment, the illuminating beam 7.1 is undeflected when directed onto the X-ray field. For example, the term "undeflected" does not preclude the use of lenses for correcting the illuminating beam within a range of up to 15°.

In one exemplary embodiment, the LEDs are disposed between the X-ray source 5.1 and the diaphragm 4.1. The illuminating beam 7.1 of the LEDs is limited by the diaphragm 4.1. The beam field of the illuminating beam 7.1 on the surface of the patient and/or on the object table 2.1 is substantially congruent with the X-ray field of the X-ray beam 11.1. The LEDs are disposed outside the X-ray beam 11.1. For example, the LEDs are distributed over the X-ray beam's 11.1 outer circumference. Both the X-ray beam and the LEDs are protected from damage from each other. According to one exemplary embodiment, the LEDs are disposed on a common ring mount 10.

FIG. 3 illustrates a ring mount 10. The ring mount 10 includes individual LEDs 6. The X-ray source 5.1 and the X-ray beam 11.1 are shown in cross section at the level of the ring mount 10. As shown in FIG. 3, the ring mount 10 is embodied and mounted in such a way that the X-ray beam 11.1 can pass through the center of the ring without being hindered. The ring mount 10 is on the X-ray source 5.1.

According to another exemplary embodiment, as shown in FIG. 4, an X-ray apparatus 1.2 includes at least one LED 6.2 mounted on a filter array 3. Alternatively, a plurality of LEDs may also be mounted to increase the brightness. The filter array 3 is mounted between the X-ray source 5.2 and the diaphragm 4.2 and moves individual filters 8.1; 8.2; and 8.3 into the X-ray beam. The filters 8.1; 8.2; and 8.3 filter out frequencies not needed for the particular X-ray image to be made.

In one exemplary embodiment, the at least one LED 6.2 is positioned in the filter array 3. The at least one LED 6.2 can be used instead of a filter 8.1; 8.2; 8.3, and is pivotable (swivelable) out of the X-ray beam 11.2. When illuminating the X-ray field, the filter array 3 is pivoted (swiveled), so that the at least one LED 6.2 is located in the beam path of the X-ray beam 11.2. The illuminating beam 7.2 on the surface of the object table 2.2 is substantially congruent with the X-ray beam 11.2. The at least one LED 6.2 may be pivotable (swivable) out of the X-ray beam 11.2 by rotation of the filter array 3 about its longitudinal axis. When the X-ray image is being made, the required filters 8.1; 8.2; and 8.3 can be pivoted (swiveled) into the beam path.

FIG. 5 illustrates a filter array 3. For example, the filter array 3 is used in the mammographic X-ray apparatus 1 shown in FIG. 4. The filter array 3 includes four mounts for filters or LEDs. According to one exemplary embodiment, three individual filters 8.1; 8.2; and 8.3 are inserted into mounts, and at least one LED 6.2 is disposed in the other mount. The present embodiments are not limited to this arrangement. For example, any combination of filters and LEDs can be used in the filter array.

While the invention has been described above by reference to various embodiments, it should be understood that many changes and modifications can be made without departing from the scope of the invention. It is therefore intended that the foregoing detailed description be regarded as illustrative rather than limiting, and that it be understood that it is the following claims, including all equivalents, that are intended to define the spirit and scope of this invention.

The invention claimed is:

1. An X-ray apparatus for making X-ray images of a patient, the X-ray apparatus comprising:
   an X-ray source operable to generate an X-ray beam which is limited by a diaphragm, and
   an illuminating beam, generated by an indicator in the form of LEDs, which illuminate, a corresponding X-ray field on a surface of a patient,
   wherein at least one LED is disposed between the X-ray source and the diaphragm, wherein the illuminating beam of the LED is aimed in an undeflected fashion at the X-ray field; and
   wherein the at least one LED is pivotable out of the X-ray beam.

2. The X-ray apparatus as defined by claim 1, having a filter array between the X-ray source and the diaphragm, wherein the at least one LED is mounted on the filter array.

3. The X-ray apparatus as defined by claim 2, wherein the at least one LED is positionable in the filter array.

4. The X-ray apparatus as defined by claim 3, wherein the at least one LED is pivotable out of the X-ray beam by rotation of the filter array about a longitudinal axis of the filter array.

5. The X-ray apparatus as defined by claim 2, wherein the filter array comprises at least one LED and at least one filter.

6. The X-ray apparatus as defined by claim 5, wherein the at least one LED is pivotable out of the X-ray beam by rotation of the filter array about a longitudinal axis of the filter array.

7. The X-ray apparatus as defined by claim 1, wherein the X-ray apparatus is a mammographic X-ray apparatus.

* * * * *